United States Patent [19]
Barriere et al.

[11] Patent Number: 5,965,527
[45] Date of Patent: *Oct. 12, 1999

[54] CYCLOSPORIN COMPOUNDS, THEIR PREPARATION AND THE PHARMACEUTICAL COMPOSITIONS WHICH CONTAIN THEM

[75] Inventors: Jean-Claude Barriere, Bures sur Yvette; Georges Bashiardes, Thiais; Jean-Christophe Carry, Meudon; Michel Evers, La Queue en Brie; Bruno Filoche, Creteil; Jean-Pierre Leconte, Brunoy; Serge Mignani, Chatenay-Malabry, all of France

[73] Assignee: Rhone-Poulenc Rorer, S.A., Antony Cedex, France

[*] Notice: This patent is subject to a terminal disclaimer.

[21] Appl. No.: 08/996,699

[22] Filed: Dec. 23, 1997

[30] Foreign Application Priority Data

Dec. 24, 1996 [FR] France ................................. 96 15956

[51] Int. Cl.$^6$ .............................. A61K 37/02; C07K 5/12
[52] U.S. Cl. .................................. 514/11; 514/9; 530/317
[58] Field of Search ................................ 530/317; 514/9, 514/11

[56] References Cited

U.S. PATENT DOCUMENTS

| | | | |
|---|---|---|---|
| 4,703,033 | 10/1987 | Seebach | 514/11 |
| 4,771,122 | 9/1988 | Seebach | 514/11 |
| 4,814,323 | 3/1989 | Andrieu et al. | 514/11 |

FOREIGN PATENT DOCUMENTS

| | | |
|---|---|---|
| 0484281 | 5/1992 | European Pat. Off. . |
| 95111162 | 7/1995 | European Pat. Off. . |
| WO 97/04005 | 2/1997 | WIPO . |

OTHER PUBLICATIONS

Billich et al , J. of Virology, Apr. 1995, pp. 2451–2461.
Papageorgiou et al., "Anti HIV–1 Activity of a Hydrophilic Cyclosporin Derivative With Improved Binding Affinity to Cyclophilin A," Bioorganic & Medicinal Chemistry Letters, 6(1):23–26 (1996).
Mikol et al., "The Role of Water Molecules in the Structure–Based Design of (5–Hydroxynorvaline)–2–cyclosporin: Synthesis, Biological Activity, and Crystallographic Analysis With Cyclophilin A," J. Med. Chem., 38(17):3361–3367 (1995).

*Primary Examiner*—Cecilia J. Tsang
*Attorney, Agent, or Firm*—Finnegan, Henderson, Farabow, Garrett & Dunner, L.L.P.

[57] ABSTRACT

A cyclosporin compound of the formula (I):

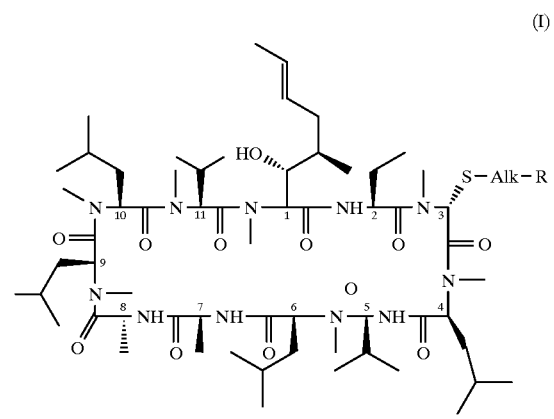

wherein Alk and R are as defined herein, or a pharmaceutically acceptable salt thereof, which derivatives are is useful in the treatment and/or prophylaxis of retrovirus infections.

21 Claims, No Drawings

CYCLOSPORIN COMPOUNDS, THEIR PREPARATION AND THE PHARMACEUTICAL COMPOSITIONS WHICH CONTAIN THEM

The technology involved in this application is related to that disclosed in the following co-pending U.S. applications, filed on even date herewith:

(1) Title: Novel Cyclosporin Compounds, Their Preparation and the Pharmaceutical Compositions Which Contain Them
   Inventors: Jean-Claude Barriere, Georges Bashiardes, Jean-Christophe Carry, Michel Evers, Bruno Filoche, and Serge Mignani
   Attorney Docket No.: 03806.0420 U.S. patent application Ser. No. 08/997,612, filed Dec. 23, 1997.

(2) Title: Cyclosporin Compound, Its Preparation and the Pharmaceutical Compositions Which Contain It
   Inventors: Jean-Claude Barriere, Georges Bashiardes, Jean-Christophe Carry, Michel Evers, Bruno Filoche, and Serge Mignani
   Attorney Docket No.: 03806.0419 U.S. patent application Ser. No. 08/997,613, filed Dec. 23, 1997.

The specifications of these related applications are hereby specifically incorporated by reference.

The present invention relates to cyclosporin compounds of general formula (I):

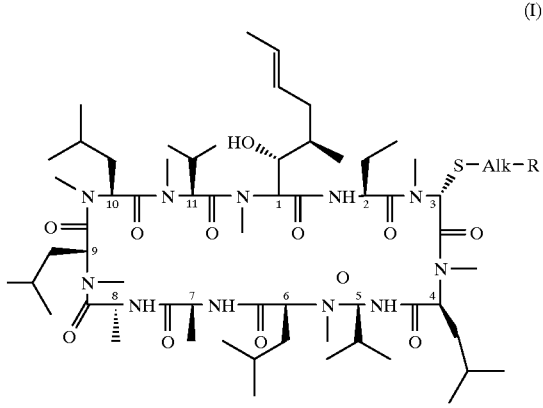

(I)

to their salts, to their preparation and to the pharmaceutical compositions which contain them.

The inventive compounds are useful in the treatment and/or prophylaxis of retrovirus infections, and more particularly of AIDS (acquired immunodeficiency syndrome) and of associated syndromes [ARC (AIDS related complex)]. The inventive compounds exhibit the advantage of being very weakly immunosuppressing.

Cyclosporin compounds modified at the 3-position have been previously described as immunosuppressants, in European Patent EP 194,972.

It has now been found that the cyclosporin compounds of formula (I), in which:

Alk represents an alkylene radical containing 2 to 6 straight- or branched-chain carbon atoms or a cycloalkylene radical containing 3 to 6 carbon atoms, and R represents
  either a carboxyl or alkyloxycarbonyl radical,
  or an —$NR_1R_2$ radical in which $R_1$ and $R_2$, which are identical or different, represent a hydrogen atom or an alkyl, alkenyl (2 to 4C), cycloalkyl (3 to 6C) or optionally substituted (by a halogen atom, alkyloxy, alkyloxycarbonyl, amino, alkylamino or dialkylamino) phenyl radical, or represent a benzyl or heterocyclyl radical, wherein the heterocyclyl radical is saturated or unsaturated and contains 5 or 6 ring members and 1 to 3 heteroatoms, preferably chosen from nitrogen, oxygen and sulphur; or in which $R_1$ and $R_2$ form, with the nitrogen atom to which they are attached, a saturated or unsaturated heterocycle containing 4 to 6 ring members, which heterocycle can contain another heteroatom chosen from nitrogen, oxygen and sulphur, optionally substituted by an alkyl, phenyl or benzyl radical, or a radical of formula (I'):

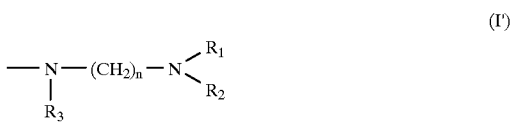

(I')

in which $R_1$ and $R_2$ are defined as above, $R_3$ represents a hydrogen atom or an alkyl radical, and n is an integer from 2 to 4;

wherein the alkyl portions or radicals defined above are straight or branched and contain 1 to 4 carbon atoms;

and their pharmaceutically acceptable salts, when they exist, are particularly preferred due to their powerful activity and their very weak immunosuppressing nature.

In the formula (I), when $R_1$ and/or $R_2$ represent a heterocyclyl radical, such radical can advantageously be chosen from pyridyl, tetrahydropyridyl, piperidyl, imidazolyl, oxazolyl and thiazolyl.

When $R_1$ and $R_2$ form a heterocyclyl with the nitrogen atom to which they are attached, by way of example, the heterocyclyl radical can be chosen from azetidinyl, piperidyl, piperazinyl, N-methylpiperazinyl, N-phenylpiperazinyl, N-benzylpiperazinyl, pyridyl, imidazolyl, morpholino, thiomorpholino, tetrahydropyridyl, methyltetrahydropyridyl (for example 4-methyltetrahydropyridyl) and phenyltetrahydropyridyl (for example 4-phenyltetrahydropyridyl).

According to the present invention, the compounds of general formula (I) can be obtained by reaction of a disulphide of formula (II):

R-Alk-S—S-Alk-R   (II)

in which R and Alk are defined as above, the functional groups of which that are capable of interfering with the reaction have, if appropriate, been protected beforehand using protective radicals, with an activated form of cyclosporin A, and then, if appropriate, the protective radical(s) is (are) removed.

The activated form of cyclosporin A is understood to mean a form activated on the sarcosine at the 3-position. This activated form of cyclosporin A is preferably prepared in situ. Activation is generally carried out under an inert atmosphere, by treatment with an organometallic derivative, in particular a lithium derivative, such as n-butyllithium, lithium diisopropylamide or a mixture, for example. It is also possible to prepare the activated form of cyclosporin A in liquid ammonia in the presence of an alkali metal amide, for example, sodium or lithium, at a temperature ranging from −32 to −38° C. in an ether, in particular tetrahydrofuran, t-butyl ethyl ether or a mixture.

The addition of the disulphide of formula (II) is advantageously carried out in an organic solvent, such as a hydrocarbon, for example, hexane, or an ether, for example, diethyl ether, tetrahydrofuran or t-butyl methyl ether, at a temperature ranging from −78 to 0° C. It is sometimes preferable to carry out the operation under nitrogen.

When the substituents of the R radical can interfere with the reaction, it is preferable to protect them beforehand with compatible radicals which can be put in place and removed without affecting the remainder of the molecule. Moreover, the hydroxyl radical present on the cyclosporin can optionally be protected by any group which does not interfere with the reaction.

By way of example, the protective groups can be chosen from the radicals described by T. W. Greene, Protective Groups in Organic Synthesis, J. Wiley-Interscience Publication (1991), or by McOmie, Protective Groups in Organic Chemistry, Plenum Press (1973).

The disulphide of formula (II) can be prepared according to or by analogy with the methods described in the examples.

The novel cyclosporin compounds of formula (I) can be purified, if appropriate, by physical methods, such as crystallization or chromatography.

The cyclosporin compounds according to the invention in which R is carboxyl can be converted into metal salts or into addition salts with a nitrogenous base according to the methods known per se. These salts can be obtained by the action of a metal base, for example, alkali metal or alkaline-earth metal, of ammonia or of an amine on a product according to the invention, in an appropriate solvent, such as water or an alcohol. The resulting salt precipitates after optional concentration of the solution; it is separated by filtration.

Mention may be made, as examples of pharmaceutically acceptable salts, of the salts with alkali metals, for example, sodium, potassium or lithium, or with alkaline-earth metals, for example, magnesium or calcium, the ammonium salt or the salts of nitrogenous bases, for example, ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine or dibenzylamine.

The cyclosporin compounds according to the invention in which R is $NR_1R_2$ can be converted into addition salts with acids by the known methods. It is understood that these salts also come within the scope of the present invention.

Mention may be made, as examples of addition salts with pharmaceutically acceptable acids, of the salts formed with inorganic acids, e.g., hydrochlorides, hydrobromides, sulphates, nitrates or phosphates, or with organic acids, e.g., succinates, fumarates, tartrates, acetates, propionates, maleates, citrates, methanesulphonates, ethanesulphonates, p-toluenesulfonates, isethionates or embonates, or with substitution derivatives of these compounds.

The novel cyclosporin compounds according to the present invention are particularly useful in the prophylaxis and treatment of retrovirus diseases and more particularly of AIDS and of associated syndromes. Prophylaxis is understood to mean in particular the treatment of subjects who have been exposed to HIV viruses, in particular asymptomatic seropositives who present the risk of developing the disease in the months or years to come after the primary infection.

The products according to the invention display an antiretrovirus activity at concentrations devoid of any cytotoxic or cytostatic effect.

The activity of the products of formula (I) has been demonstrated in the techniques described by Pauwells et al., J. Virol. Meth., 20, 309 (1988) and by O. Schwatz et al., AIDS Research and Human Retroviruses, 4(6), 441–48 (1988) and cited by J. F. Mayaux et al., Proc. Nat. Acad. Sci. U.S.A., 91, 3564–68 (1994), the disclosures of which are incorporated herein by reference. In these techniques, the products according to the invention have proved to be active at concentrations of 3 to 350 nM ($IC_{50}$).

The products of formula (I) in which:
Alk represents an alkylene radical containing 2 to 6 straight- or branched-chain carbon atoms; and
R represents an —$NR_1R_2$ radical in which $R_1$ and $R_2$, which are identical or different, represent a hydrogen atom or an alkyl, alkenyl (2 to 4 C) or optionally substituted (by a halogen atom, alkyloxy, alkyloxycarbonyl, amino, alkylamino or dialkylamino) phenyl radical or represent a benzyl radical; or in which $R_1$ and $R_2$ form, with the nitrogen atom to which they are attached, a saturated or unsaturated heterocycle containing 4 to 6 ring members, which heterocycle can contain another heteroatom chosen from nitrogen, oxygen and sulphur, optionally substituted by an alkyl radical;
wherein the alkyl portions or radicals defined above are straight or branched and contain 1 to 4 carbon atoms, and their pharmaceutically acceptable salts, when they exist, are particularly preferred.

More preferred are the cyclosporin compounds of formula (I) in which:
Alk represents an alkylene radical containing 2 to 5 straight- or branched-chain carbon atoms; and
R represents an —$NR_1R_2$ radical in which $R_1$ and $R_2$, which are identical or different, represent a hydrogen atom or an alkyl, allyl, phenyl or benzyl radical; or in which $R_1$ and $R_2$ form, with the nitrogen atom to which they are attached, a heterocycle chosen from azetidinyl, piperidyl, piperazinyl, N-methylpiperazinyl, N-phenylpiperazinyl, N-benzylpiperazinyl, imidazolyl, morpholino, tetrahydropyridyl, methyltetrahydropyridyl and phenyltetrahydropyridyl;
wherein the alkyl portions or radicals defined above are straight or branched and containing 1 to 4 carbon atoms, and their pharmaceutically acceptable salts, when they exist.

Among these more preferred products, particularly preferred are the cyclosporin derivatives listed below:
-[(R)-2-(N,N-diethylamino)ethylthio-Sar]$^3$-cyclosporin A;
-[(R)-2-(N,N-dimethylamino)ethylthio-Sar]$^3$-cyclosporin A;
-[(R)-2-(1-piperidyl)ethylthio-Sar]$^3$-cyclosporin A;
-[(R)-2-(N-methyl-N-i-propylamino)ethylthio-Sar]$^3$-cyclosporin A; and
-[(R)-2-(N-methyl-N-t-butylamino)ethylthio-Sar]$^3$-cyclosporin A;
and their pharmaceutically acceptable salts, when they exist.

The following examples, given without implied limitation, illustrate the present invention.

EXAMPLE 1

[(R)-2-(N,N-Diethylamino)ethylthio-Sar]$^3$-cyclosporin A methanesulphonate was prepared according to the following method:

15.6 cm$^3$ of a 1.6M solution of n-butyllithium in hexane were added over 20 minutes to a solution, cooled to a temperature in the region of −10° C. and under nitrogen, of 3.53 cm$^3$ of diisopropylamine (distilled beforehand over calcium hydride) in 45 cm³ of tetrahydrofuran (distilled beforehand over sodium), the temperature being maintained at 0° C. The mixture was stirred at 0° C. for 20 minutes and was then cooled to a temperature in the region of −78° C. The solution thus obtained was transferred, under nitrogen, via a transfer tube, onto a solution of 2 g of cyclosporin A in 40 cm³ of tetrahydrofuran cooled beforehand to a temperature in the region of −78° C., the temperature being maintained at approximately −75° C. The resulting mixture was stirred at −75° C. for 10 minutes and then 6.3 cm³ of a 1.6M solution of n-butyllithium in hexane were added over 4 minutes. Stirring was maintained for 20 minutes and then 8.8 g of di[2-(N,N-diethylamino)ethyl]disulphide were added over 2 minutes, the temperature being maintained at approximately −75° C. The mixture was stirred at a temperature in the region of −75° C. for 30 minutes and then at 0° C. for 18 h. A mixture of 50 cm³ of ice-cold distilled water and of 36% aqueous hydrochloric acid was poured onto the reaction mixture in order to obtain a pH in the region of 7, the mixture was then separated by settling and the aqueous phase was washed with 30 cm³ of diethyl ether. The organic extracts were combined, washed with 50 cm³ of saturated sodium chloride solution, dried over sodium sulphate, filtered and concentrated under reduced pressure (2.7 kPa) at a temperature in the region of 40° C. The solid obtained was purified by 2 successive flash chromatography operations on a silica column (0.04–0.063 mm) (eluent: methanol/water/dichloromethane 14/2/84 by volume, then dichloromethane/methanol 93/7 by volume), 10-cm³ fractions were collected. The fractions containing the expected product were combined and concentrated under reduced pressure (2.7 kPa) at a temperature in the region of 40° C. to give 0.245 g of [(R)-2-(N,N-diethylamino)ethylthio-Sar]³-cyclosporin A in the form of a white solid.

0.245 g of [(R)-2-(N,N-diethylamino)ethylthio-Sar]³-cyclosporin A was dissolved, with stirring, in 15 cm³ of diethyl ether in a round-bottomed flask. After filtration, 15 mg of methanesulphonic acid, in solution in 2 cm³ of diethyl ether, were added over 30 seconds. The white precipitate obtained was filtered off and washed with 3 times 2 cm³ of diethyl ether and then with 2 cm³ of pentane. 0.067 g of [(R)-2-(N,N-diethylamino)ethylthio-Sar]³-cyclosporin A methanesulphonate was thus obtained in the form of a white solid melting at 155° C. (dec.).

¹H N.M.R. spectrum (400 MHz, CDCl₃, δ in ppm): 1.24 (d, J=7 Hz, 3H, 8β CH₃), 1.31 (d, J=7.5 Hz, 3H, 7β CH₃), 1.31 (t, J=7 Hz, 6H, CH₃ of the ethyl of the 2-diethylaminoethylthio at 3α), 1.60 (d, J=5 Hz, 3H, CH₃ at 1γ), 2.38 (mt, 1H, 5β CH), 2.66, 2.75, 3.08, 3.10, 3.22, 3.41 and 3.46 (7 s, respectively 6H, 3H, 3H, 3H, 3H, 3H and 3H, 7 NCH₃ and CH₃ of the methanesulphonate), from 2.90 to 3.35 (unresolved peak, 8H, SCH₂CH₂N of the 2-diethylaminoethylthio at 3α and NCH₂ of the ethyl of the 2-diethylaminoethylthio at 3α), 3.76 (mt, 1H, 1β CH), 4.48 (mt, 1H, 7α CH), 4.64 (t, J=9 Hz, 1H, 5α CH), 4.81 (mt, 1H, 8α CH), from 4.95 to 5.05 (mt, 2H, 2α CH and α CH of a leucine), 5.06 (d, J=11 Hz, 1H, 11α CH), 5.18 (dd, J=12 and 4 Hz, 1H, α CH of a leucine), from 5.20 to 5.35 (mt, 2H, CH=CH), 5.41 (d, J=6 Hz, 1H, 1α CH), 5.67 (dd, J=10 and 4 Hz, 1H, α CH of a leucine), 5.90 (s, 1H, 3α CH), 7.17 (d, J=9 Hz, 1H, CONH at 5), 7.39 (d, J=8 Hz, 1H, CONH at 8), 7.68 (d, J=7.5 Hz, 1H, CONH at 7), 8.04 (d, J=9.5 Hz, 1H, CONH at 2).

Di[2-(N,N-diethylamino)ethyl]disulphide was prepared according to the method described in H. Gilman, J. Am. Chem. Soc. (1945), 67, 1846, the disclosure of which is incorporated herein by reference.

EXAMPLE 2

[(R)-2-(N,N-Dimethylamino)ethylthio-Sar]³-cyclosporin A was prepared according to the following method:

117 cm³ of a 1.6M solution of n-butyllithium in hexane were added over 30 minutes to a solution, cooled to a temperature in the region of −5° C. and under nitrogen, of 26.5 cm³ of diisopropylamine (distilled beforehand over calcium hydride) in 300 cm³ of tetrahydrofuran (distilled beforehand over sodium), the temperature being maintained at 0° C. The mixture was stirred at 0° C. for 20 minutes and was then cooled to a temperature in the region of −78° C. The solution thus obtained was transferred, under nitrogen, via a transfer tube, onto a solution of 15 g of cyclosporin A in 270 cm³ of tetrahydrofuran cooled beforehand to a temperature in the region of −76° C., the temperature being maintained at approximately −70° C. The resulting mixture was stirred at −78° C. for 10 minutes and then 47 cm³ of a 1.6M solution of n-butyllithium in hexane were added over 10 minutes. Stirring was continued for 5 minutes and then 52 g of commercially available di[2-(N,N-dimethylamino)ethyl]disulphide were slowly added, the temperature being maintained at approximately −75° C. The mixture was stirred at a temperature in the region of −78° C. for 30 minutes and then at 0° C. for 18 h. 120 cm³ of ice-cold distilled water, to which 80 cm³ of 12N hydrochloric acid have been added, were poured onto the reaction mixture, kept stirring at −20° C., in order to obtain a pH in the region of 7, the mixture was then separated by settling and the aqueous phase was washed with 100 cm³ of ethyl acetate. The organic extracts were combined, washed with a saturated sodium chloride solution, dried over sodium sulphate, filtered and concentrated under reduced pressure (2.7 kPa) at a temperature in the region of 40° C. The solid obtained was dissolved in 200 cm³ of toluene and 1000 cm³ of distilled water to which 12N hydrochloric acid had been added in order to bring the pH to 2. The phases were separated by settling. The aqueous phase was washed again with 100 cm³ of toluene and the toluene phases were combined. The latter were washed with 200 cm³ of distilled water and acidified to a pH in the region of 3. The aqueous phases were combined, 200 cm³ of toluene were added and then neutralization was carried out with an aqueous sodium bicarbonate solution. The organic phase was separated by settling and the aqueous phase was washed with 100 cm³ of toluene. The organic phases were combined, dried over sodium sulphate, filtered and concentrated under reduced pressure (2.7 kPa) at a temperature in the region of 40° C. to give a solid which was purified by flash chromatography on a silica column (0.04–0.063 mm) (eluent: dichloromethane/methanol 93.5/6.5 by volume), 35-cm³ fractions were collected. The fractions containing the expected product were combined and concentrated under reduced pressure (2.7 kPa) at a temperature in the region of 40° C. to give a solid which was triturated in 30 cm³ of pentane. After filtration, 1.94 g of [(R)-2-(N,N-dimethylamino)ethylthio-Sar]³-cyclosporin A were obtained in the form of a white solid that melted at approximately 140° C.

¹H N.M.R. spectrum (400 MHz, CDCl₃, δ in ppm): 1.28 (d, J=7 Hz, 3H, 8β CH₃), 1.37 (d, J=7.5 Hz, 3H, 7β CH₃), 1.63 (mt, 3H, CH₃ at 1γ), 2.25 (s, 6H, N(CH₃)₂ of the 2-dimethylaminoethylthio at 3α), 2.40 (mt, 1H, 5β CH), from 2.50 to 2.80 (unresolved peak, 4H, SCH₂CH₂N of the 2-dimethylaminoethylthio at 3α), 2.71, 3.13, 3.14, 3.28, 3.46 and 3.52 (6 s, respectively 6H, 3H, 3H, 3H, 3H and 3H, 7 NCH₃), 3.65 (d, J=6 Hz, 1H, OH at 1β), 3.78 (mt, 1H, 1β CH), 4.56 (mt, 1H, 7α CH), 4.67 (t, J=9 Hz, 1H, 5α CH), 4.85 (mt, 1H, 8α CH), 4.99 (dd, J=9 and 6 Hz, 1H, α CH of a leucine), from 5.00 to 5.15 (mt, 2H, 2α CH and α CH of a leucine), 5.15 (d, J=11 Hz, 1H, 11α CH), 5.25 (dd, J=12 and 4 Hz, 1H, α CH of a leucine), from 5.30 to 5.45 (mt, 2H, CH═CH), 5.51 (d, J=6 Hz, 1H, 1α CH), 5.72 (dd, J=10.5 and 4 Hz, 1H, α CH of a leucine), 6.02 (s, 1H, 3α CH), 7.18 (d, J=8 Hz, 1H, CONH at 8), 7.35 (d, J=9 Hz, 1H, CONH at 5), 7.68 (d, J=7.5 Hz, 1H, CONH at 7), 7.96 (d, J=9.5 Hz, 1H, CONH at 2).

The methanesulphonate salt of [(R)-2-(N,N-dimethylamino)ethylthio-Sar]$^3$-cyclosporin A was prepared in the following way:

360 mg of [(R)-2-(N,N-dimethylamino)ethylthio-Sar]$^3$-cyclosporin A were dissolved, with stirring, in 6 cm$^3$ of diethyl ether in a round-bottomed flask and then 24 mg of methanesulphonic acid, in solution in 1 cm$^3$ of diethyl ether, were added over 30 seconds. The white precipitate obtained was filtered off and washed with 3 times 2 cm$^3$ of diethyl ether and then with 5 cm$^3$ of pentane. After drying at 50° C. under reduced pressure (40 kPa), 0.328 mg of [(R)-2-(N,N-dimethylamino)ethylthio-Sar]$^3$-cyclosporin A methanesulphonate was thus obtained in the form of a white solid that melted at 155° C. (dec.).

$^1$H N.M.R. spectrum (400 MHz, (CD$_3$)$_2$SO, δ in ppm): 1.21 (d, J=7.5 Hz, 3H, 8β CH$_3$), 1.29 (d, J=7.5 Hz, 3H, 7β CH$_3$), 1.69 (d, J=6.5 Hz, 3H, CH$_3$ at 1γ), 1.99 (mt, 1H, 5β CH), 2.35 (s, 3H, CH$_3$ of the methanesulphonate), from 2.45 to 2.70 (mt, 2H, SCH$_2$ of the 2-dimethylaminoethylthio at 3α), 2.64, 2.80, 2.86, 2.93, 2.99 and 3.17 (6 s, respectively 3H, 6H, 9H, 3H, 3H and 3H, 7 NCH$_3$ and NCH$_3$ of the 2-dimethylamino-ethylthio at 3α), from 3.25 to 3.40 (unresolved peak, 2H, CH$_2$N of the 2-dimethylaminoethylthio at 3α), 3.99 (mt, 1H, 1β CH), 4.15 (mt, 1H, 7α CH), 4.26 (t, J=9 Hz, 1H, 5α CH), 4.42 (broad s, 1H, OH at 1β), 4.79 (mt, 1H, 8αCH), 4.89 (mt, 1H, 2α CH), from 5.00 to 5.15 (mt, 1H, α CH of a leucine), 5.11 (d, J=11 Hz, 1H, 11α CH), 5.23 (mt, 2H, 1α CH and α CH of a leucine), 5.33 (dd, J=10 and 5 Hz, 1H, α CH of a leucine), from 5.30 to 5.50 and 5.62 (2 mts, each 1H, CH═CH), 5.48 (dd, J=11 and 5 Hz, 1H, α CH of a leucine), 6.87 (s, 1H, 3α CH), 7.64 (d, J=7.5 Hz, 1H, CONH at 7), 8.24 (d, J=9.5 Hz, 1H, CONH at 2), 8.28 (d, J=8 Hz, 1H, CONH at 8), 8.68 (d, J=9 Hz, 1H, CONH at 5), 9.28 (unresolved peak, 1H, SO$_3$H of the methanesulphonate).

EXAMPLE 3

[(R)-2-(1-Piperidyl)ethylthio-Sar]$^3$-cyclosporin A was prepared according to the following method:

31 cm$^3$ of a 1.6M solution of n-butyllithium in hexane were added dropwise to a solution, cooled to a temperature in the region of 0° C. and under argon, of 7.0 cm$^3$ of diisopropylamine in 40 cm$^3$ of tetrahydrofuran. The mixture was stirred at 0° C. for 20 minutes, was then cooled to a temperature in the region of −78° C. and a solution of 4.0 g of cyclosporin A and of 6.0 cm$^3$ of 1,3-dimethyl-3,4,5,6-tetrahydro-2(1H)-pyrimidinone in 20 cm$^3$ of tetrahydrofuran under argon, cooled beforehand to a temperature in the region of −78° C., was added dropwise. The resulting mixture was stirred at a temperature in the region of −40° C. for 20 minutes and then at a temperature in the region of −78° C. for 1 h and then a solution of 13.8 g of di[2-(1-piperidyl)ethyl]disulphide in 20 cm$^3$ of tetrahydrofuran was added dropwise. The mixture was subsequently stirred at a temperature in the region of −78° C. for 10 minutes and was then allowed to reheat to a temperature in the region of 20° C. It was then treated with 100 cm$^3$ of water. The aqueous phase was extracted 3 times with 100 cm$^3$ of ethyl acetate and then the organic extracts were combined, washed 4 times with 50 cm$^3$ of water, dried over magnesium sulphate and concentrated under reduced pressure (2.7 kPa) at a temperature in the region of 40° C. The oil obtained was chromatographed on a column containing 1.6 kg of silica (0.02–0.05 mm) eluted with ethyl acetate at atmospheric pressure, 75-cm$^3$ fractions were collected. The fractions containing the expected product were combined and concentrated under reduced pressure (2.7 kPa) at a temperature in the region of 40° C. The residue was dissolved in 20 cm$^3$ of ethyl acetate, filtered through paper and then reconcentrated under the same conditions. The residue obtained was taken up in 20 cm$^3$ of ethyl ether, reconcentrated in the same way and then dried to constant weight. 0.4 g of [(R)-2-(1-piperidyl)ethylthio-Sar]$^3$-cyclosporin A was thus obtained in the form of a straw-yellow solid that melted at 132° C.

$^1$H N.M.R. spectrum (400 MHz, CDCl$_3$, δ in ppm): 1.30 (d, J=7 Hz, 3H, 8β CH$_3$), 1.37 (d, J=7.5 Hz, 3H, 7β CH$_3$), 1.65 (d, J=5 Hz, 3H, CH$_3$ at 1γ), from 1.90 to 3.10 (mt, 14H, CH$_2$ of SCH$_2$CH$_2$Npiperidine at 3α), 2.47 (mt, 1H, 5β CH), 2.70 2.72, 3.13, 3.18, 3.27, 3.45 and 3.52 (7 s, each 3H, 7 NCH$_3$), 3.77 (mt, 1H, 1β CH), 4.55 (mt, 1H, 7α CH), 4.65 (t, J=9 Hz, 1H, 5α CH), 4.86 (mt, 1H, 8α CH), 4.99 (dd, J=9 and 6 Hz, 1H, α CH of a leucine), from 5.00 to 5.15 (mt, 2H, 2α CH and α CH of a leucine), 5.15 (d, J=11 Hz, 1H, 11α CH), 5.24 (dd, J=12 and 4 Hz, 1H, α CH of a leucine), from 5.25 to 5.45 (mt, 2H, CH═CH), 5.50 (d, J=6 Hz, 1H, 1α CH), 5.72 (dd, J=10.5 and 4 Hz, 1H, α CH of a leucine), 6.22 (s, 1H, 3α CH), 7.18 (d, J=8 Hz, 1H, CONH at 8), 7.38 (d, J=9 Hz, 1H, CONH at 5), 7.70 (d, J=7.5 Hz, 1H, CONH at 7), 7.95 (d, J=9.5 Hz, 1H, CONH at 2).

Di[2-(1-piperidyl)ethyl]disulphide was prepared according to the method described by R. C. Fuson in J. Org. Chem., 11, 487 (1946), the disclosure of which is incorporated by reference herein.

EXAMPLE 4

[(R)-2-(N-Methyl-N-i-propylamino)ethylthio-Sar]$^3$-cyclosporin A was prepared according to the following method:

100 mg of sodium metal and then 100 mg of ferric nitrate were added to 100 cm$^3$ of ammonia maintained at a temperature in the region of −33° C. As soon as the blue coloration of the mixture had disappeared, 1.1 g of sodium metal were added over 15 minutes. The mixture was stirred at −33° C. for 2 hours, a solution of 3.6 g of cyclosporin A in 60 cm$^3$ of tetrahydrofuran was added dropwise over approximately 20 minutes and then a solution of 3.1 g of di[2-(N-methyl-N-i-propylamino)ethyl]disulphide in 15 cm$^3$ of tetrahydrofuran was added over 15 minutes. The reaction mixture was stirred at a temperature in the region of −33° C. for 1 hour and then 3 g of solid ammonium chloride were added portionwise. The ammonia was allowed to evaporate with stirring, the temperature of the mixture changed from −33 to 25° C. over 12 hours. The mixture was diluted with 100 cm$^3$ of diethyl ether and then filtered. The solid was rinsed with 100 cm$^3$ in total of diethyl ether. The combined organic phases were concentrated under reduced pressure (2.7 kPa) at a temperature in the region of 40° C. The solid obtained (6.3 g) was purified by chromatography on a silica column (0.020–0.045 mm) (eluent: ethyl acetate/methanol 4/1 by volume), 50-cm$^3$ fractions were collected. The fractions containing the expected product (fractions 32 to 48) were combined and concentrated under reduced pressure (2.7 kPa) at a temperature in the region of 40° C.

to give 0.640 g of a colourless lacquer which, treated with 30 cm³ of distilled water, gave, after filtration and drying at a temperature in the region of 40° C., 0.390 g of [(R)-2-(N-methyl-N-i-propylamino)ethylthio-Sar]³-cyclosporin A in the form of an off-white solid that melted at approximately 70° C.

¹H N.M.R. spectrum (400 MHz, CDCl₃, δ in ppm): 1.26 (d, J=7.5 Hz, 3H, 8β CH₃), 1.37 (d, J=7.5 Hz, 3H, 7β CH₃), 2.18 (s, 3H, NCH₃ of the 2-(N-isopropylamino)ethylthio at 3α), from 2.55 to 2.75 (mt, the 4H corresponding to the SCH₂CH₂N of the 2-(N-methyl-N-isopropylamino) ethylthio at 3α), 2.71, 2.72, 3.12, 3.14, 3.27, 3.45 and 3.51 (7 s, each 3H, the 7 NCH₃), 2.83 (mt, 1H, NCH of the 2-(N-methyl-N-isopropylamino)-ethylthio at 3α), 3.65 (d, J=6 Hz, 1H, OH at 1β), 3.77 (mt, 1H, 1β CH), 4.54 (mt, 1H, 7α CH), 4.65 (broad t, J=9 Hz, 1H, 5α CH), 4.84 (mt, 1H, 8α CH), 4.97 (dd, J=10.5 and 6 Hz, 1H, α CH of a leucine), from 5.00 to 5.10 (mt, 2H, α CH of a leucine and 2α CH), 5.13 (d, J=11 Hz, 1H, 11α CH), 5.24 (dd, J=11.5 and 4 Hz, 1H, α CH of a leucine), 5.33 (mt, 2H, CH=CH), 5.50 (d, J=6 Hz, 1H, 1α CH), 5.71 (dd, J=10.5 and 4 Hz, 1H, α CH of a leucine), 5.97 (s, 1H, 3α CH), 7.17 (d, J=8 Hz, 1H, CONH at 8), 7.34 (d, J=9 Hz, 1H, CONH at 5), 7.66 (d, J=8 Hz, 1H, CONH at 7), 7.95 (d, J=10 Hz, 1H, CONH at 2).

Di[2-(N-methyl-N-i-propylamino)ethyl]disulphide was prepared in the following way:

60 cm³ of a 5N aqueous sodium hydroxide solution were added to a solution of 20 g of 2-(N-i-propyl-N-methylamino)ethanethiol in 150 cm³ of diethyl ether and then a stream of air was passed through the reaction mixture for 12 hours at a temperature in the region of 20° C. The mixture was extracted by means of 150 cm³ in total of diethyl ether. The combined organic phases were washed with 100 cm³ of distilled water, dried over magnesium sulphate and then concentrated under reduced pressure (2.7 kPa) at a temperature in the region of 40° C. to result in 11.1 g of di[2-(N-methyl-N-i-propylamino)ethyl]disulphide in the form of a colourless oil.

2-(N-Isopropyl-N-methylamino)ethanethiol was prepared according to the following method:

A solution of 115 cm³ of N-i-propyl-N-methylamine and of 44 cm³ of ethylene sulphide in 400 cm³ of diethyl ether was heated at a temperature in the region of reflux for 36 hours. Fractional distillation of the reaction mixture under reduced pressure (2.5 kPa) resulted in 43 g of 2-(N-i-propyl-N-methylamino)ethanethiol in the form of a colourless oil that boiled at approximately 60° C. at 2.5 kPa.

EXAMPLE 5

[(R)-2-(N-Methyl-N-t-butylamino)ethylthio-Sar]³-cyclosporin A was prepared according to the following method:

100 mg of sodium metal and then 100 mg of ferric nitrate were added to 100 cm³ of ammonia maintained at a temperature in the region of −33° C. As soon as the blue coloration of the mixture had disappeared, 1.0 g of sodium metal was added over 30 minutes. The mixture was stirred at −33° C. for 1 hour, a solution of 3.6 g of cyclosporin A in 50 cm³ of tetrahydrofuran was added dropwise over approximately 30 minutes and then a solution of 3.5 g of di[2-(N-methyl-N-t-butylamino)ethyl]disulphide in 15 cm³ of tetrahydrofuran was added over 15 minutes. The reaction mixture was stirred at a temperature in the region of −33° C. for 1 hour and then 3 g of solid ammonium chloride were added portionwise. The ammonia was allowed to evaporate with stirring, the temperature of the mixture changing from −33 to 25° C. over 12 hours. The mixture was diluted with 100 cm³ of diethyl ether and then filtered. The solid was rinsed with 300 cm³ in total of diethyl ether. The combined organic phases were concentrated under reduced pressure (2.7 kPa) at a temperature in the region of 40° C. The solid obtained was triturated with 250 cm³ of pentane and then filtered off. The residual solid (6 g) was purified by chromatography on a silica column (0.020–0.045 mm) (eluent:ethyl acetate/methanol 4/1 by volume), 100-cm³ fractions being collected. The fraction containing the expected product (fraction 9) was concentrated under reduced pressure (2.7 kPa) at a temperature in the region of 40° C. to give 0.500 g of a solid which was stirred with 30 cm³ of pentane and gave, after filtration and drying at a temperature in the region of 40° C., 0.200 g of [(R)-2-(N-methyl-N-t-butylamino)ethylthio-Sar]³-cyclosporin A in the form of an off-white solid that melted at approximately 130° C.

¹H N.M.R. spectrum (400 MHz, CDCl₃, δ in ppm): 1.05 (s, the 9H corresponding to the C(CH₃)₃), 1.26 (d, J=7.5 Hz, 3H, 8β CH₃), 1.36 (d, J=7.5 Hz, 3H, 7β CH₃), 1.63 (d, J=5 Hz, 3H, 1η CH₃), 2.19 (s, 3H, NCH₃ of the 2-(N-tert-butyl-N-methylamino)ethylthio at 3α), from 2.55 to 2.80 (mt, the 4H corresponding to the SCH₂CH₂N of the 2-(N-tert-butyl-N-methylamino)ethylthio at 3α), 2.70, 2.72, 3.12, 3.13, 3.26, 3.45 and 3.51 (7 s, each 3H, the 7 NCH₃), 3.61 (d, J=6.5 Hz, 1H, OH at 1β), 3.76 (mt, 1H, 1β CH), 4.54 (mt, 1H, 7α CH), 4.65 (broad t, J=9 Hz, 1H, 5α CH), 4.84 (mt, 1H, 8α CH), 4.97 (dd, J=10 and 6 Hz, 1H, α CH of a leucine), from 5.00 to 5.10 (mt, 2H, α CH of a leucine and 2α CH), 5.13 (d, J=11 Hz, 1H, 11α CH), 5.24 (dd, J=10.5 and 4 Hz, 1H, α CH of a leucine), 5.34 (mt, 2H, CH=CH), 5.49 (d, J=6 Hz, 1H, 1α CH), 5.71 (dd, J=10.5 and 4 Hz, 1H, α CH of a leucine), 5.90 (s, 1H, 3α CH), 7.16 (d, J=8 Hz, 1H, CONH at 8), 7.33 (d, J=9 Hz, 1H, CONH at 5), 7.66 (d, J=8 Hz, 1H, CONH at 7), 7.96 (d, J=10 Hz, 1H, CONH at 2).

Di[2-(N-methyl-N-t-butylamino)ethyl]disulphide was prepared in the following way:

0.1 cm³ of a 1N aqueous sodium hydroxide solution was added to a solution of 28.7 g of 2-(N-t-butyl-N-methylamino)ethanethiol in 190 cm³ of methanol and then a stream of air was passed through the mixture for 60 hours at a temperature in the region of 20° C. The methanol was removed under reduced pressure (2.7 kPa). The residual oil was dissolved in 400 cm³ of diethyl ether. The organic phase was dried over magnesium sulphate, filtered and then concentrated under reduced pressure (2.7 kPa) at a temperature in the region of 40° C. to result in 26.6 g of di[2-(N-methyl-N-t-butylamino)ethyl]disulphide in the form of a yellow oil.

2-(N-t-Butyl-N-methylamino)ethanethiol was prepared according to the following method:

A solution of 125 cm³ of N-t-butyl-N-methylamine and of 50 g of ethylene episulphide in 750 cm³ of t-butyl methyl ether was stirred for 48 hours at a temperature in the region of reflux. The mixture was concentrated under reduced pressure (10 kPa) at a temperature in the region of 35° C. Fractional distillation of the reaction mixture under reduced pressure (5.8 kPa) resulted in 28.7 g of 2-(N-t-butyl-N-methylamino)ethanethiol in the form of a colourless oil that boiled between 84 and 86° C. at 5.8 kPa.

EXAMPLE 6

[(R)-2-(1-Imidazolyl)ethylthio-Sar]³-cyclosporin A was prepared according to the following method:

100 mg of sodium metal and then 100 mg of ferric nitrate were added to 80 cm³ of ammonia maintained at a temperature in the region of −33° C. As soon as the blue coloration of the mixture had disappeared, 0.82 g of sodium metal was added over 15 minutes. The mixture was stirred at −33° C. for 15 minutes, a solution of 2.4 g of cyclosporin A in 10 cm$^3$ of tetrahydrofuran was subsequently added dropwise over approximately 15 minutes and then 5 g of solid di[2-(1-imidazolyl)ethyl]disulphide were added portionwise over 15 minutes. The reaction mixture was stirred at a temperature in the region of −33° C. for 3 hours and then 3.4 g of solid ammonium chloride were added portionwise. The ammonia was allowed to evaporate with stirring, the temperature of the mixture changed from −33 to 25° C. over 12 hours. The mixture was diluted with 100 cm$^3$ of distilled water. The organic phase was separated by settling and the aqueous phase was washed with 3 times 50 cm$^3$ of ethyl acetate. The combined organic phases were dried over magnesium sulphate, filtered and then concentrated under reduced pressure (2.7 kPa) at a temperature in the region of 40° C. The beige foam thus obtained (2.25 g) was purified by chromatography on a silica column (0.020–0.045 mm) (eluent:ethyl acetate/methanol 19/1 by volume), 20-cm$^3$ fractions were collected. The fractions containing the expected product were concentrated under reduced pressure (2.7 kPa) at a temperature in the region of 40° C. and gave 0.520 g of a solid. This solid, triturated with 50 cm$^3$ of pentane, gave, after filtration and drying at a temperature in the region of 40° C., 0.420 g of a solid which was purified by chromatography on a second silica column (0.020–0.045 mm) (eluent:ethyl acetate/methanol 4/1 by volume). The fractions containing the expected product were concentrated under reduced pressure (2.7 kPa) at a temperature in the region of 40° C. The residual solid was stirred with 10 cm$^3$ of pentane to give, after filtration and drying at a temperature in the region of 40° C., 0.245 g of [(R)-2-(1-imidazolyl)ethylthio-Sar]$^3$-cyclosporin A in the form of a yellow solid that melted at approximately 208° C.

$^1$H N.M.R. spectrum (400 MHz, CDCl$_3$, at a temperature of 333 K, δ in ppm): 1.26 (d, J=7.5 Hz, 3H, 8β CH$_3$), 1.36 (d, J=7.5 Hz, 3H, 7β CH$_3$), 1.63 (d, J=5 Hz, 3H, 1η CH$_3$), 2.72, 3.07, 3.15, 3.25, 3.40 and 3.50 (6 s, respectively 6H, 3H, 3H, 3H, 3H and 3H, the 7 NCH$_3$), from 3.80 to 3.95 (mt, 2H, 1β CH and OH at 1β), 4.16 (mt, 2H, NCH$_2$), 4.51 (mt, 1H, 7α CH), 4.71 (broad t, J=9 Hz, 1H, 5α CH), 4.86 (mt, 1H, 8α CH), from 4.95 to 5.10 (mt, 3H, α CH of two leucines and 2α CH), 5.17 (d, J=11 Hz, 1H, 11α CH), 5.22 (dd, J=11.5 and 4 Hz, 1H, α CH of a leucine), 5.35 (mt, 2H, CH=CH), 5.42 (d, J=6 Hz, 1H, 1α CH), 5.72 (dd, J=10.5 and 4 Hz, 1H, α CH of a leucine), 5.82 (s, 1H, 3α CH), 6.93, 7.10 and 7.54 (3 broad s, each 1H, aromatic H of the imidazole), 7.12 (d, J=8 Hz, 1H, CONH at 8), 7.19 (d, J=9 Hz, 1H, CONH at 5), 7.53 (mt, 1H, CONH at 7), 7.87 (d, J=10 Hz, 1H, CONH at 2).

Di[2-(1-imidazolyl)ethyl]disulphide was prepared in the following way:

32.3 cm$^3$ of triethylamine, followed by a solution of 14.59 g of iodine in 68 cm$^3$ of diethyl ether, were added dropwise over 10 minutes to a solution of 15 g of 2-(1-imidazolyl) ethanethiol in 200 cm$^3$ of dichloromethane cooled to 0° C. The mixture was stirred for 30 minutes at a temperature in the region of 20° C. and then concentrated under reduced pressure (2.7 kPa) at a temperature in the region of 40° C. The pasty residue was triturated in the presence of 50 cm$^3$ of isopropanol. The solid formed was filtered off and rinsed with 25 cm$^3$ in total of isopropanol to give a first crop of di[2-(1-imidazolyl)ethyl] disulphide. The combined organic phases were concentrated under reduced pressure (2.7 kPa) at a temperature in the region of 40° C. The pasty residue was triturated in the presence of 50 cm$^3$ of ethyl acetate. The solid formed was filtered off to give a second crop of di[2-(1-imidazolyl)ethyl]disulphide. The two crops of di[2-(1-imidazolyl)ethyl]disulphide were combined and dried under vacuum (10 kPa) at a temperature in the region of 20° C. to result in 14.2 g of di[2-(1-imidazolyl)ethyl]disulphide.

2-(1-Imidazolyl)ethanethiol was prepared in the following way:

A solution of 28.34 g of 2-(1-imidazolyl)ethylisothiourea hydrochloride and of 18.56 g of sodium hydroxide in 300 cm$^3$ of distilled water was heated at reflux for 150 minutes. After having been brought back to a temperature in the region of 20° C., the mixture was acidified by addition of concentrated hydrochloric acid (20 cm$^3$) and then brought to pH=7 by addition of a saturated sodium bicarbonate solution. The mixture was extracted with 600 cm$^3$ in total of ethyl acetate. The combined organic phases were washed with 100 cm$^3$ in total of distilled water, filtered, dried over magnesium sulphate and then concentrated under reduced pressure (2.7 kPa) at a temperature in the region of 40° C. to result in 15.0 g of 2-(1-imidazolyl)ethanethiol in the form of a yellow oil.

2-(1-Imidazolyl)ethylisothiourea hydrochloride was prepared in the following way:

44.2 cm$^3$ of thionyl chloride were added dropwise over 30 minutes to a solution of 30 g of 2-hydroxy-1-(1-imidazolyl) ethane in 300 cm$^3$ of dichloromethane and then the mixture was brought to a temperature in the region of reflux for 16 hours. The mixture was concentrated under reduced pressure (2.7 kPa) at a temperature in the region of 40° C. The pasty residue was treated with 100 cm$^3$ of dichloromethane and then concentrated under reduced pressure (2.7 kPa) at a temperature in the region of 40° C. This stage was repeated twice. A suspension of 34.9 g of crude 2-chloro-1-(1-imidazolyl)ethane hydrochloride thus obtained and 15.93 g of thiourea in 125 cm$^3$ of dimethylformamide was heated at a temperature in the region of 110° C. for 90 minutes. The mixture was cooled to a temperature in the region of 20° C. The yellow solid formed was subsequently filtered off, rinsed with 100 cm$^3$ in total of diethyl ether and dried under vacuum (10 kPa) at a temperature in the region of 40° C. to result in 28.34 g of 2-(1-imidazolyl)ethylisothiourea hydrochloride in the form of a solid that melted at a temperature in the region of 206° C.

2-Hydroxy-1-(1-imidazolyl)ethane was prepared in the following way:

A solution of 68 g of imidazole in 250 cm$^3$ of dimethylformamide was added over 30 minutes to a suspension of 30 g of sodium hydride (at 50% in mineral oil) in 250 cm$^3$ of dimethylformamide. The mixture was stirred for 90 minutes at a temperature in the region of 20° C. and then a solution of 50.5 g of 2-chloroethanol in 50 cm$^3$ of dimethylformamide was added over one hour. The mixture was stirred for 12 hours at a temperature in the region of 20° C. and then filtered. The filtrate was treated with 100 cm$^3$ of distilled water and then concentrated under reduced pressure (2.7 kPa) at a temperature in the region of 55° C. The pasty residue was taken up in 150 cm$^3$ of petroleum ether, the liquid phase was separated by settling and the residue was triturated for one hour with 100 cm$^3$ of isopropanol. The precipitate formed was filtered off and the filtrate was concentrated under reduced pressure (2.7 kPa) at a temperature in the region of 40° C. The residual oil (113.1 g) was distilled under reduced pressure (5 kPa) and resulted in 105.7 g of 2-hydroxy-(1-imidazolyl)ethane in the form of a yellow oil that distilled at a temperature of 180–183° C. at 5 kPa.

EXAMPLE 7

By carrying out the preparations in a way analogous to the methods described in Examples 1 to 3, the following products can be prepared:

-[(R)-2-aminoethylthio-Sar]³-cyclosporin A;
-[(R)-2-(N-methylamino)ethylthio-Sar]³-cyclosporin A;
-[(R)-2-(N-ethylamino)ethylthio-Sar]³-cyclosporin A;
-[(R)-2-(N-i-propylamino)ethylthio-Sar]³-cyclosporin A;
-[(R)-2-(N-t-butylamino)ethylthio-Sar]³-cyclosporin A;
-[(R)-2-(N-phenylamino)ethylthio-Sar]³-cyclosporin A;
-[(R)-2-(N-benzylamino)ethylthio-Sar]³-cyclosporin A;
-[(R)-2-(N-methyl-N-ethylamino)ethylthio-Sar]³-cyclosporin A;
-[(R)-2-(N-methyl-N-allylamino)ethylthio-Sar]³-cyclosporin A;
-[(R)-2-(N-methyl-N-phenylamino)ethylthio-Sar]³-cyclosporin A;
-[(R)-2-(N-methyl-N-benzylamino)ethylthio-Sar]³-cyclosporin A;
-[(R)-2-(N,N-di-i-propylamino)ethylthio-Sar]³-cyclosporin A;
-[(R)-2-(N,N-diallylamino)ethylthio-Sar]³-cyclosporin A;
-[(R)-3-aminopropylthio-Sar]³-cyclosporin A;
-[(R)-3-(N-methylamino)propylthio-Sar]³-cyclosporin A;
-[(R)-3-(N-ethylamino)propylthio-Sar]³-cyclosporin A;
-[(R)-3-(N-i-propylamino)propylthio-Sar]³-cyclosporin A;
-[(R)-3-(N-t-butylamino)propylthio-Sar]³-cyclosporin A;
-[(R)-3-(N-phenylamino)propylthio-Sar]³-cyclosporin A;
-[(R)-3-(N-benzylamino)propylthio-Sar]³-cyclosporin A;
-[(R)-3-(N-methyl-N-ethylamino)propylthio-Sar]³-cyclosporin A;
-[(R)-3-(N-methyl-N-i-propylamino)propylthio-Sar]³-cyclosporin A;
-[(R)-3-(N-methyl-N-t-butylamino)propylthio-Sar]³-cyclosporin A;
-[(R)-3-(N-methyl-N-allylamino)propylthio-Sar]³-cyclosporin A;
-[(R)-3-(N-methyl-N-phenylamino)propylthio-Sar]³-cyclosporin A;
-[(R)-3-(N-methyl-N-benzylamino)propylthio-Sar]³-cyclosporin A;
-[(R)-2-(N,N-dimethylamino)ethylthio-Sar]³-cyclosporin A;
-[(R)-3-(N,N-diethylamino)propylthio-Sar]³-cyclosporin A;
-[(R)-3-(N,N-di-i-propylamino)propylthio-Sar]³-cyclosporin A;
-[(R)-3-(N,N-diallylamino)propylthio-Sar]³-cyclosporin A;
-[(R)-3-(1-piperidyl)propylthio-Sar]³-cyclosporin A;
-[(R)-4-aminobutylthio-Sar]³-cyclosporin A;
-[(R)-4-(N-methylamino)butylthio-Sar]³-cyclosporin A;
-[(R)-4-(N-ethylamino)butylthio-Sar]³-cyclosporin A;
-[(R)-4-(N-i-propylamino)butylthio-Sar]³-cyclosporin A;
-[(R)-4-(N-t-butylamino)butylthio-Sar]³-cyclosporin A;
-[(R)-4-(N-phenylamino)butylthio-Sar]³-cyclosporin A;
-[(R)-4-(N-benzylamino)butylthio-Sar]³-cyclosporin A;
-[(R)-4-(N-methyl-N-ethylamino)butylthio-Sar]³-cyclosporin A;
-[(R)-4-(N-methyl-N-i-propylamino)butylthio-Sar]³-cyclosporin A;
-[(R)-4-(N-methyl-N-t-butylamino)butylthio-Sar]³-cyclosporin A;
-[(R)-4-(N-methyl-N-allylamino)butylthio-Sar]³-cyclosporin A;
-[(R)-4-(N-methyl-N-phenylamino)butylthio-Sar]³-cyclosporin A;
-[(R)-4-(N-methyl-N-benzylamino)butylthio-Sar]³-cyclosporin A;
-[(R)-4-(N,N-dimethylamino)butylthio-Sar]³-cyclosporin A;
-[(R)-4-(N,N-diethylamino)butylthio-Sar]³-cyclosporin A;
-[(R)-4-(N,N-di-i-propylamino)butylthio-Sar]³-cyclosporin A;
-[(R)-4-(N,N-diallylamino)butylthio-Sar]³-cyclosporin A;
-[(R)-4-(1-piperidyl)butylthio-Sar]³-cyclosporin A;
-[(R)-2-amino-2-methylpropylthio-Sar]³-cyclosporin A;
-[(R)-2-(N,N-dimethylamino)-2-methylpropylthio-Sar]³-cyclosporin A;
-[(R)-2-(N,N-diethylamino)-2-methylpropylthio-Sar]³-cyclosporin A;
-[(R)-2-(1-piperidyl)-2-methylpropylthio-Sar]³-cyclosporin A;
-[(R)-3-amino-3-methylbutylthio-Sar]³-cyclosporin A;
-[(R)-3-(N,N-dimethylamino)-3-methylbutylthio-Sar]³-cyclosporin A;
-[(R)-3-(N,N-diethylamino)-3-methylbutylthio-Sar]³-cyclosporin A;
-[(R)-3-(1-piperidyl)-3-methylbutylthio-Sar]³-cyclosporin A;
-[(R)-2-(1-morpholino)ethylthio-Sar]³-cyclosporin A;
-[(R)-2-(1-azetidino)ethylthio-Sar]³-cyclosporin A;
-{(R)-2-[1-(methylpiperazino)]ethylthio-Sar}³-cyclosporin A;
-{(R)-2-[1-(4-phenylpiperazino)]ethylthio-Sar}³-cyclosporin A;
-{(R)-2-[1-(4-benzylpiperazino)]ethylthio-Sar}³-cyclosporin A;
-{(R)-2-[1-(4-methyl-1,2,3,6-tetrahydropyridyl)]ethylthio-Sar}³-cyclosporin A;
-{(R)-2-[1-(4-phenyl-1,2,3,6-tetrahydropyridyl)]ethylthio-Sar}³-cyclosporin A;
-[(R)-3-(1-morpholino)propylthio-Sar]³-cyclosporin A;
-[(R)-3-(1-(azetidino)propylthio-Sar]³-cyclosporin A;
-{(R)-3-[1-(4-methylpiperazino)]propylthio-Sar}³-cyclosporin A;
-{(R)-3-[1-(4-phenylpiperazino)]propylthio-Sar}³-cyclosporin A;
-{(R)-3-[1-(4-benzylpiperazino)]propylthio-Sar}³-cyclosporin A;
-{(R)-3-[1-(4-methyl-1,2,3,6-tetrahydropyridyl)]propylthio-Sar}³-cyclosporin A; and
-{(R)-3-[1-(4-methyl-1,2,3,6-tetrahydropyridyl)]propylthio-Sar}³-cyclosporin A; and their pharmaceutically acceptable salts, when they exist.

The present invention also relates to pharmaceutical compositions containing at least one product of general formula (I), if appropriate in the salt form, either used alone or in the form of a combination with one or more compatible and pharmaceutically acceptable carriers, such as diluents or adjuvants, or with another anti-retrovirus agent, optionally intended for the treatment of AIDS, or an antiviral, immunomodulating or antimicrobial agent.

The composition according to the invention is capable of keeping alive cells infected with a retrovirus, such as, for example, the HIV, and thus of reducing progression towards AIDS or of decreasing its seriousness in subjects already infected by reducing the mortality of infected cells. The compositions can be used orally, parenterally, rectally or in aerosols.

The pharmaceutical compositions can be used curatively or preventively in subjects exhibiting immunodeficiency and/or infected by a retrovirus. Of course, the makeup of these compositions will be suited to the specific case of the digestive system of the immunodepressed subjects.

Use may be made, as solid compositions for oral administration, of tablets, pills, hard gelatin capsules, powders or granules. In these compositions, the active product according to the invention is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavouring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate.

These compositions can also contain adjuvants, in particular wetting, isotonizing, emulsifying, dispersing and stabilizing agents.

Sterilization can be carried out in several ways, for example using a bacteriological filter, by radiation or by heating. They can also be prepared in the form of sterile solid compositions which can be dissolved at the time of use in sterile water or any other injectable sterile mixture.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle with a particle size of 30 to 80 μm, for example dextran, mannitol or lactose.

In human therapeutics, the doctor will determine the posology which he considers most appropriate according to a preventive or curative treatment and according to the age, weight, stage of the infection and other factors specific to the subject to be treated. Generally, doses are between 5 and 30 mg/kg by the oral route for an adult.

In addition, it has been shown that cyclosporin compounds of formula (I) display a synergistic effect or at least an addition effect when they are combined with other antiviral agents which are active with respect to retroviruses. The present invention also relates to synergistic combinations which contain at least one cyclosporin compound of formula (I) and/or, if appropriate, their salts and an active principle known for its activity with respect to retroviruses.

The agents known for their activity with respect to retroviruses which can be combined are chosen from agents which are compatible and inert with respect to the cyclosporin derivative of general formula (I), both in the category of pharmacological treatments and in the category of alternative treatments, such as gene and cell or antisense therapy. Without implied limitation, these agents constituting the various therapeutic classes are chosen, for example, from nucleoside reverse transcriptase inhibitors (NRTI) and non-nucleoside reverse transcriptase inhibitors (NNRTI) [zidovudine (AZT), didanosine (DDI), dideoxycytidine (DDC), d4T, ribavirin, 3TC, nevirapin, and the like], from protease inhibitors [such as, for example, Saquinavir, Ritonavir, Indinavir and Nelfinavir], integrase inhibitors [such as AR177], from therapy gene inhibitors targeting the regulatory proteins of HIV replication, such as inhibitors of the rev protein [such as, for example, Rev M10], or nucleocapsid inhibitors [such as, for example, DIBAs], from inhibitors targeting the specific messenger RNA transcripts of all the HIVs, such as, for example, the antisense ones [such as GEM92, GPI-2A and the like], from inhibitors of the family of modulators of cellular dNTP [such as hydroxyurea], from cytokine inhibitors [such as TNF], from inhibitors of entry of HIVs [such as T20, SPC-3, and the like], and from agents constituting therapeutic classes used in vaccinal approaches, both by biotechnology [such as HIVAC-1e, ALVAC, and the like] and by compounds acting with respect to the immune response [such as RG-8394].

The cyclosporin compound of Example 2 in particular displays a particularly advantageous effect when it is combined with AZT, ddI, Saquinavir and/or ribavirin.

The pharmaceutical compositions comprising such combinations, optionally in the presence of pharmaceutically acceptable excipients, are also within the scope of the present invention.

The following example illustrates a composition according to the invention.

Formulation Example

A formulation was prepared which was administered by the oral route and which had the following composition:

| | |
|---|---|
| [(R)-2-(N,N-Dimethylamino)ethylthio-Sar]³-cyclosporin A | 250 mg |
| Magnesium stearate | 3 mg |
| Acidsol | 15 mg |
| Colloidal silica | 2 mg |
| Lactose | 130 mg |

What is claimed is:
1. A cyclosporin compound of formula (I)

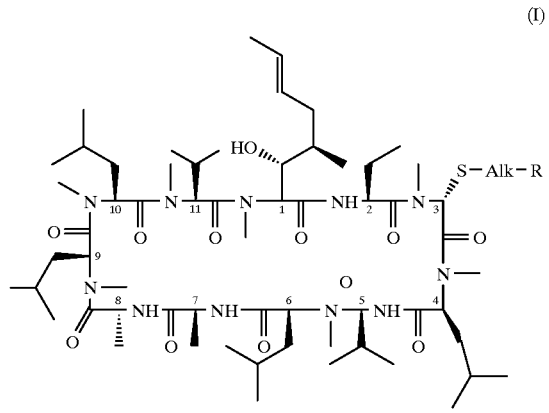

in which:
Alk represents a $C_{2-6}$ straight chain or branched alkylene radical or a $C_{3-6}$ cycloalkylene radical, and
R represents
a carboxyl radical,
an alkyloxycarbonyl radical,
an —$NR_1R_2$ radical in which $R_1$ and $R_2$, which are identical or different, represent a hydrogen atom or an alkyl, $C_{2-4}$ alkenyl, $C_{3-6}$ cycloalkyl or optionally substituted phenyl radical, wherein said phenyl radical may be substituted by a halogen atom, or an alkyloxy, alkyloxycarbonyl, amino, alkylamino or dialkylamino radical, or represent a benzyl or heterocyclyl radical, wherein the heterocyclyl radical is saturated or unsaturated and contains 5 or 6 ring members and from 1 to 3 heteroatoms; or in which $R_1$ and $R_2$ form, together with the nitrogen atom to which they are attached, a saturated or unsaturated heterocycle containing 4 to 6 ring members, wherein said saturated or unsaturated heterocycle may optionally contain a further heteroatom selected from nitrogen, oxygen and sulphur atoms, and wherein said saturated or unsaturated heterocycle is optionally substituted by an alkyl, phenyl or benzyl radical, or a radical of the formula (I'):

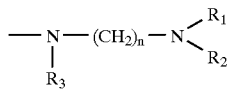

(I')

in which $R_1$ and $R_2$ are as defined above, $R_3$ represents a hydrogen atom or an alkyl radical, and n is an integer from 2 to 4, wherein the alkyl portions or radicals defined above are straight chain or branched and contain from 1 to 4 carbon atoms;

or a pharmaceutically acceptable salt thereof.

2. A cyclosporin compound according to claim 1, in which:

Alk represents a $C_{2-6}$ straight chain or branched alkylene radical, and

R represents an —$NR_1R_2$ radical in which $R_1$ and $R_2$, which are identical or different, represent a hydrogen atom or an alkyl, $C_{2-4}$ alkenyl or optionally substituted phenyl radical, wherein said phenyl radical may be substituted by a halogen atom, or an alkyloxy, alkyloxycarbonyl, amino, alkylamino or dialkylamino radical or represent a benzyl radical; or in which $R_1$ and $R_2$ form, together with the nitrogen atom to which they are attached, a saturated or unsaturated heterocycle containing 4 to 6 ring members, wherein said saturated or unsaturated heterocycle may optionally contain a further heteroatom selected from nitrogen, oxygen and sulphur, and wherein said saturated or unsaturated heterocycle is optionally substituted by an alkyl radical;

or a pharmaceutically acceptable salt thereof.

3. A cyclosporin compound according to claim 1, wherein:

Alk represents a $C_{2-5}$ straight chain or branched alkylene radical, and

R represents an —$NR_1R_2$ radical in which $R_1$ and $R_2$, which are identical or different, represent a hydrogen atom or an alkyl, allyl, phenyl or benzyl radical; or in which $R_1$ and $R_2$ form, together with the nitrogen atom to which they are attached, a heterocycle selected from azetidinyl, piperidyl, piperazinyl, N-methylpiperazinyl, N-phenylpiperazinyl, N-benzylpiperazinyl, imidazolyl, morpholino, tetrahydropyridyl, methyltetrahydropyridyl and phenyltetrahydropyridyl;

or a pharmaceutically acceptable salt thereof.

4. A cyclosporin compound according to claim 1, which is [(R)-2-(N,N-diethylamino)ethylthio-Sar]³-cyclosporin A, or a pharmaceutically acceptable salt thereof.

5. A cyclosporin compound according to claim 1, which is [(R)-2-(N,N-dimethylamino)ethylthio-Sar]³-cyclosporin A, or a pharmaceutically acceptable salt thereof.

6. A cyclosporin compound according to claim 1, which is [(R)-2-(1-piperidyl)ethylthio-Sar]³-cyclosporin A, or a pharmaceutically acceptable salt thereof.

7. A cyclosporin compound according to claim 1, which is [(R)-2-(N-methyl-N-i-propylamino)ethylthio-Sar]³-cyclosporin A, or a pharmaceutically acceptable salt thereof.

8. A cyclosporin compound according to claim 1, which is [(R)-2-(N-methyl-N-t-butylamino)ethylthio-Sar]³-cyclosporin A, or a pharmaceutically acceptable salt thereof.

9. A process for preparing a cyclosporin compound of formula (I) according to claim 1, said process comprising reacting a disulphide of the formula:

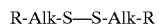

in which R and Alk are defined according to claim 1, with an activated form of cyclosporin A, in which any functional group in said cyclosporin A capable of interfering with said reaction has been protected with a protecting radical, removing, if appropriate, the protecting radical(s), and optionally converting the product of said reaction into a salt.

10. A pharmaceutical composition, said composition comprising at least one cyclosporin compound of formula (I) according to claim 1, said cyclosporin compound being present alone or in combination with a compatible and pharmaceutically acceptable carrier.

11. A pharmaceutical composition according to claim 10, wherein said cyclosporin compound is present in combination with at least one antiviral, immunodulating or antimicrobial active principle.

12. A combination comprising at least one cyclosporin compound of formula (I) according to claim 1 and further comprising at least one anti-retroviral agent.

13. A combination according to claim 12, wherein said at least one anti-retroviral agent is AZT, ddI, Saquinavir or ribavirin.

14. A combination, said combination comprising [(R)-2-(N,N-dimethylamino)ethylthio-Sar]³-cyclosporin A or a pharmaceutically acceptable salt thereof and further comprising at least one anti-retroviral agent.

15. A combination according to claim 14, wherein said at least one anti-retroviral agent is AZT, ddI, Saquinavir or ribavirin.

16. A synergistic combination comprising at least one cyclosporin compound of formula (I) according to claim 1 and further comprising at least one anti-retroviral agent.

17. A method for treating a retrovirus, said method comprising administering to a host in need of said prevention or treatment an effective amount of a cyclosporin compound of formula (I) or a salt thereof according to claim 1.

18. A method according to claim 17, wherein said retrovirus is AIDS or an AIDS associated syndrome.

19. A method according to claim 17, wherein said effective amount of said cyclosporin compound of formula (I) or salt thereof is a concentration of 10 to 350 nM.

20. A compound selected from:
-[(R)-2-aminoethylthio-Sar]³-cyclosporin A;
-[(R)-2-(N-methylamino)ethylthio-Sar]³-cyclosporin A;
-[(R)-2-(N-ethylamino)ethylthio-Sar]³-cyclosporin A;
-[(R)-2-(N-i-propylamino)ethylthio-Sar]³-cyclosporin A;
-[(R)-2-(N-t-butylamino)ethylthio-Sar]³-cyclosporin A;
-[(R)-2-(N-phenylamino)ethylthio-Sar]³-cyclosporin A;
-[(R)-2-(N-benzylamino)ethylthio-Sar]³-cyclosporin A;
-[(R)-2-(N-methyl-N-ethylamino)ethylthio-Sar]³-cyclosporin A;
-[(R)-2-( N-methyl-N-allylamino)ethylthio-Sar]³-cyclosporin A;

-[(R)-2-(N-methyl-N-phenylamino)ethylthio-Sar]³-cyclosporin A;
-[(R)-2-(N-methyl-N-benzylamino)ethylthio-Sar]³-cyclosporin A;
-[(R)-2-(N,N-di-i-propylamino)ethylthio-Sar]3-cyclosporin A;
-[(R)-2-(N,N-diallylamino)ethylthio-Sar]³-cyclosporin A;
-[(R)-3-aminopropylthio-Sar]³-cyclosporin A;
-[(R)-3-(N-methylamino)propylthio-Sar]³-cyclosporin A;
-[(R)-3-(N-ethylamino)propylthio-Sar]³-cyclosporin A;
-[(R)-3-(N-i-propylamino)propylthio-Sar]³-cyclosporin A;
-[(R)-3-(N-t-butylamino)propylthio-Sar]³-cyclosporin A;
-[(R)-3-(N-phenylamino)propylthio-Sar]³-cyclosporin A;
-[(R)-3-(N-benzylamino)propylthio-Sar]³-cyclosporin A;
-[(R)-3-(N-methyl-N-ethylamino)propylthio-Sar]³-cyclosporin A;
-[(R)-3-(N-methyl-N-i-propylamino)propylthio-Sar]³-cyclosporin A;
-[(R)-3-(N-methyl-N-t-butylamino)propylthio-Sar]³-cyclosporin A;
-[(R)-3-(N-methyl-N-allylamino)propylthio-Sar]³-cyclosporin A;
-[(R)-3-(N-methyl-N-phenylamino)propylthio-Sar]³-cyclosporin A;
-[(R)-3-(N-methyl-N-benzylamino)propylthio-Sar]³-cyclosporin A;
-[(R)-2-(N,N-dimethylamino)ethylthio-Sar]³-cyclosporin A;
-[(R)-3-(N,N-diethylamino)propylthio-Sar]³-cyclosporin A;
-[(R)-3-(N,N-di-i-propylamino)propylthio-Sar]³-cyclosporin A;
-[(R)-3-(N,N-diallylamino)propylthio-Sar]³-cyclosporin A;
-[(R)-3-(1-piperidyl)propylthio-Sar]³-cyclosporin A;
-[(R)-4-aminobutylthio-Sar]³-cyclosporin A;
-[(R)-4-(N-methylamino)butylthio-Sar]³-cyclosporin A;
-[(R)-4-(N-ethylamino)butylthio-Sar]³-cyclosporin A;
-[(R)-4-(N-i-propylamino)butylthio-Sar]³-cyclosporin A;
-[(R)-4-(N-t-butylamino)butylthio-Sar]³-cyclosporin A;
-[(R)-4-(N-phenylamino)butylthio-Sar]³-cyclosporin A;
-[(R)-4-(N-benzylamino)butylthio-Sar]³-cyclosporin A;
-[(R)-4-(N-methyl-N-ethylamino)butylthio-Sar]³-cyclosporin A;
-[(R)-4-(N-methyl-N-i-propylamino)butylthio-Sar]³-cyclosporin A;
-[(R)-4-(N-methyl-N-t-butylamino)butylthio-Sar]³-cyclosporin A;
-[(R)-4-(N-methyl-N-allylamino)butylthio-Sar]³-cyclosporin A;
-[(R)-4-(N-methyl-N-phenylamino)butylthio-Sar]³-cyclosporin A;
-[(R)-4-(N-methyl-N-benzylamino)butylthio-Sar]³-cyclosporin A;
-[(R)-4-(N,N-dimethylamino)butylthio-Sar]³-cyclosporin A;
-[(R)-4-(N,N-diethylamino)butylthio-Sar]³-cyclosporin A;
-[(R)-4-(N,N-di-i-propylamino)butylthio-Sar]³-cyclosporin A;
-[(R)-4-(N,N-diallylamino)butylthio-Sar]³-cyclosporin A;
-[(R)-4-(1-piperidyl)butylthio-Sar]³-cyclosporin A;
-[(R)-2-amino-2-methylpropylthio-Sar]³-cyclosporin A;
-[(R)-2-(N,N-dimethylamino)-2-methylpropylthio-Sar]³-cyclosporin A;
-[(R)-2-(N,N-diethylamino)-2-methylpropylthio-Sar]³-cyclosporin A;
-[(R)-2-(1-piperidyl)-2-methylpropylthio-Sar]³-cyclosporin A;
-[(R)-3-amino-3-methylbutylthio-Sar]³-cyclosporin A;
-[(R)-3-(N,N-dimethylamino)-3-methylbutylthio-Sar]³-cyclosporin A;
-[(R)-3-(N,N-diethylamino)-3-methylbutylthio-Sar]³-cyclosporin A;
-[(R)-3-(1-piperidyl)-3-methylbutylthio-Sar]³-cyclosporin A;
-[(R)-2-(1-morpholino)ethylthio-Sar]³-cyclosporin A;
-[(R)-2-(1-azetidino)ethylthio-Sar]³-cyclosporin A;
-{(R)-2-[1-(methylpiperazino)]ethylthio-Sar}³-cyclosporin A;
-{(R)-2-[1-(4-phenylpiperazino)]ethylthio-Sar}³-cyclosporin A;
-{(R)-2-[1-(4-benzylpiperazino)]ethylthio-Sar}³-cyclosporin A;
-{(R)-2-[1-(4-methyl-1,2,3,6-tetrahydropyridyl)]ethylthio-Sar}³-cyclosporin A;
-{(R)-2-[1-(4-phenyl-1,2,3,6-tetrahydropyridyl)]ethylthio-Sar}³-cyclosporin A;
-[(R)-3-(1-morpholino)propylthio-Sar]³-cyclosporin A;
-[(R)-3-(1-(azetidino)propylthio-Sar]³-cyclosporin A;
-{(R)-3-[1-(4-methylpiperazino)]propylthio-Sar}³-cyclosporin A;
-{(R)-3-[1-(4-phenylpiperazino)]propylthio-Sar}³-cyclosporin A;
-{(R)-3-[1-(4-benzylpiperazino)]propylthio-Sar}³-cyclosporin A;
-{(R)-3-[1-(4-methyl-1,2,3,6-tetrahydropyridyl)]propylthio-Sar}³-cyclosporin A; and
-{(R)-3-[1-(4-methyl-1,2,3,6-tetrahydropyridyl)]propylthio-Sar}³-cyclosporin A; therefor their pharmaceutically acceptable salts.

21. A cyclosporin compound of formula (I)

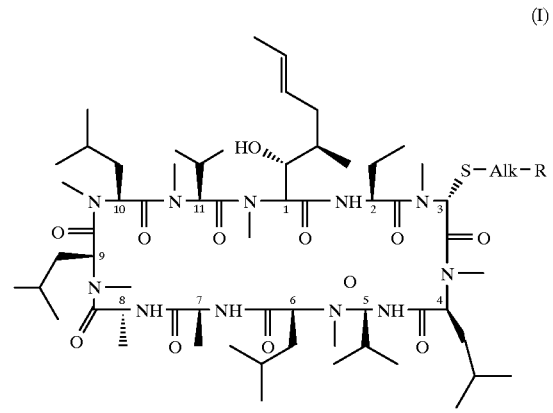

(I)

in which:
Alk represents a $C_{2-6}$ straight chain or branched alkylene radical or a $C_{3-6}$ cycloalkylene radical, and
R represents
a carboxyl radical,
an alkyloxycarbonyl radical,
an 13 $NR_1R_2$ radical in which $R_1$ and $R_2$, which are identical or different, represent a hydrogen atom or an alkyl, $C_{3-6}$ cycloalkyl or optionally substituted phenyl radical, wherein said phenyl radical may be substituted by a halogen atom, or an alkyloxy, alkyloxycarbonyl, amino, alkylamino or dialkylamino radical, or represent a benzyl or heterocyclyl radical, wherein the heterocyclyl radical is saturated or unsaturated and contains 5 or 6 ring members and from 1 to 3 heteroatoms; or in which $R_1$ and $R_2$ form, together with the nitrogen atom to which they are attached, a saturated or unsaturated heterocycle containing 5 to 6 ring members, wherein said saturated or unsaturated heterocycle may optionally contain a further heteroatom selected from nitrogen, oxygen and sulphur atoms, and wherein said saturated or unsaturated heterocycle is optionally substituted by an alkyl radical, or a radical of the formula (I'):

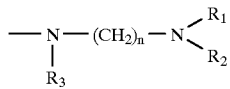

(I')

in which $R_1$ and $R_2$ are as defined above, $R_3$ represents a hydrogen atom or an alkyl radical, and n is an integer from 2 to 4, wherein the alkyl portions or radicals defined above are straight chain or branched and contain from 1 to 4 carbon atoms;

or a pharmaceutically acceptable salt thereof.

* * * * *

UNITED STATES PATENT AND TRADEMARK OFFICE
CERTIFICATE OF CORRECTION

PATENT NO. : 5,965,527
DATED : October 12, 1999
INVENTOR(S) : Jean-Claude Barriere et al.

It is certified that error appears in the above-indentified patent and that said Letters Patent is hereby corrected as shown below:

Claim 1, col. 16, line 35, after "formula (I)", insert --:--.

Claim 20, col. 19, line 5, "ethylthio-Sar]3" should read --ethylthio-Sar]$^3$--.

Claim 20, col. 20, line 28, "therefor" should read --or--.

Claim 21, col. 20, line 30, after "formula (I)", insert --:--.

Claim 21, col. 20, line 55, "an 13 NR$_1$R$_2$" should read --an -NR$_1$R$_2$--.

Signed and Sealed this

Seventeenth Day of April, 2001

*Attest:*

NICHOLAS P. GODICI

*Attesting Officer*   Acting Director of the United States Patent and Trademark Office